United States Patent [19]

Meinke et al.

[11] Patent Number: 5,350,742
[45] Date of Patent: Sep. 27, 1994

[54] AVERMECTIN DIFLUORO DERIVATIVES

[75] Inventors: Peter T. Meinke, New York, N.Y.; Helmut Mrozik, Matawan; Michael H. Fisher, Ringoes, both of N.J.

[73] Assignee: Merck & Co., Inc., Rahway, N.J.

[21] Appl. No.: 74,763

[22] Filed: Jun. 10, 1993

Related U.S. Application Data

[62] Division of Ser. No. 875,486, Apr. 29, 1992, Pat. No. 5,229,416.

[51] Int. Cl.$^5$ .................. A61K 31/365; C07D 493/22
[52] U.S. Cl. ........................... 514/28; 514/450; 549/264; 536/7.1
[58] Field of Search .......... 549/264; 536/7.1; 514/450, 28

[56] References Cited

U.S. PATENT DOCUMENTS

| | | | |
|---|---|---|---|
| 4,171,314 | 10/1979 | Chabala et al. | 260/343 |
| 4,173,571 | 11/1979 | Chabala et al. | 260/343 |
| 5,229,415 | 7/1993 | Linn et al. | 549/264 X |
| 5,229,416 | 7/1993 | Meinke et al. | 549/264 X |

FOREIGN PATENT DOCUMENTS

| | | |
|---|---|---|
| 203832 | 6/1986 | European Pat. Off. . |
| 180539 | 9/1986 | European Pat. Off. . |
| 340849 | 4/1989 | European Pat. Off. . |
| 357460 | 9/1989 | European Pat. Off. . |
| 423445 | 8/1990 | European Pat. Off. . |

*Primary Examiner*—Johann Richter
*Assistant Examiner*—Michael B. Hydorn
*Attorney, Agent, or Firm*—David L. Rose; Sylvia A. Ayler

[57] ABSTRACT

Avermectin derivatives are disclosed which incorporate two fluorine atoms at the 4' monosaccharide position, the 4" disaccharide position or the 23 position. Avermectin aglycone derivatives are also disclosed which incorporate two fluorine atoms at position 13 or 23. These difluoro avermectin analogs are derived from corresponding ketones and enones which in turn are prepared by chemical modification of naturally occurring avermectins. These compounds are used as antiparisitic, insecticidal and antihelmintic agents in humans and animals and compositions containing such compounds as the active ingredient thereof are also disclosed.

7 Claims, No Drawings

AVERMECTIN DIFLUORO DERIVATIVES

This is a division of application Ser. No. 07/875,486, filed Apr. 29, 1992 now U.S. Pat. No. 5,229,416.

BACKGROUND OF THE INVENTION

The avermectins (previously referred to as C-076 compounds) are a series of compounds produced by fermentation of avermectin producing strains of *Streptomyces avermitilis* and derivatives thereof. The morphological characteristics of the culture are completely described in U.S. Pat. No. 4,310,519. The production, isolation, and structure determination of the avermectins are fully described in Albers-Schonberg et al., *J. Am. Chem. Soc.* 1981, 103, 4216–4221 and references cited therein. The conversion of natural avermectin B1 to 22,23-dihydro-avermectin B1, the potent broad spectrum anthelminthic agent known as ivermectin, has also been described in the literature (Chabala et al., *J. Med. Chem.* 1980, 23, 1134–1136). The naturally occurring avermectins and the instant derivatives thereof have a very high degree of anthelminthic and anti-parasitic activity.

The naturally occurring avermectins are a series of macrocyclic lactones which are substituted at position 13 with a disaccharide consisting of two oleandrose residues. The preparation and properties of synthetic avermectin aglycones in which the disaccharide moiety has been removed leaving a free hydroxyl group at position 13 have been described by Mrozik et al., *J. Org. Chem.* 1982, 47, 489–492 and by Chabala et al., *J. Med. Chem.* 1980, 23, 1134–1136. The natural compounds have the following general structure:

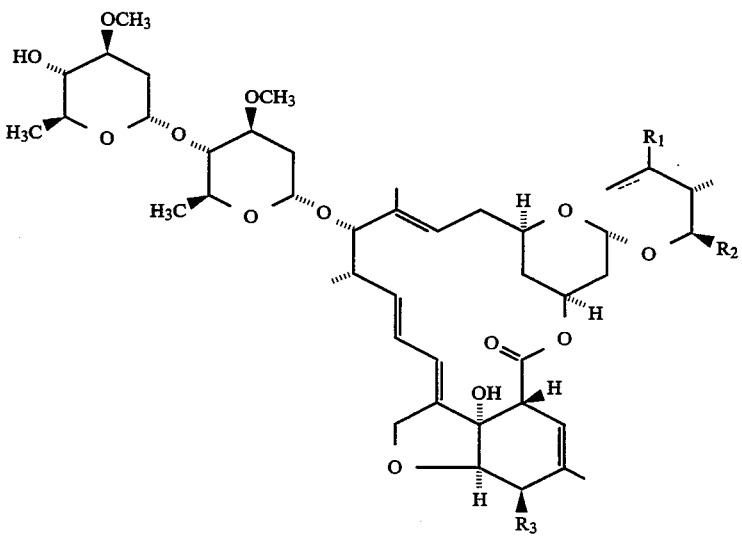

wherein the broken line at the 22,23-position indicates a single or double bond and;

$R_1$ is hydroxy and is present only when said broken line indicates a single bond;

$R_2$ is isopropyl or sec-butyl; and $R_3$ is methoxy or hydroxy.

There are eight major natural avermectin compounds, designated A1a, A1b, A2a, A2b, B1a, B1b, B2a and B2b. These designations are based on the structure of the individual compounds as shown in the following table (referring to the foregoing structural formula).

| Compound | 22,23-bond  | $R_1$ | $R_2$     | $R_3$   |
|----------|-------------|-------|-----------|---------|
| A1a      | double bond | —     | sec-butyl | —OCH₃   |
| A1b      | double bond | —     | isopropyl | —OCH₃   |
| A2a      | single bond | —OH   | sec-butyl | —OCH₃   |
| A2b      | single bond | —OH   | isopropyl | —OCH₃   |
| B1a      | double bond | —     | sec-butyl | —OH     |
| B1b      | double bond | —     | isopropyl | —OH     |
| B2a      | single bond | —OH   | sec-butyl | —OH     |
| B2b      | single bond | —OH   | isopropyl | —OH     |

The avermectins are generally isolated as mixtures of the a and b components (typically ≧180% a and ≦120% b). Such compounds differ only in the nature of the $R_2$ substituent and this minor structural difference has been found to have very little effect on the chemical reactivity or biological activity of the compounds. Thus although the a and b components can be separated from each other by chromatography this is not necessary and hence is not normally done. The presence of a mixture of a and b components may be indicated by dropping the a or b from the designation of the compound. A mixture of avermectin B1a and avermectin B1b is thus referred to as avermectin B1. Alternatively a slash(/) is inserted between the compound designations to indicate a mixture such as in "B1a/B1b".

The above structural formula is shown without a definitive stereochemistry at certain positions and with a defined stereochemistry at other positions. However, during the course of the synthetic procedures used to prepare such compounds, or using racemization or epimerization procedures known to those skilled in the art, the products of such procedures can be a mixture of stereoisomers. In particular, the stereoisomers at the 13- and 23-positions may be oriented either α- or β-representing such groups being below or above the general plane of the molecule, respectively. In each such case, and at other positions in the molecule, both the α- and β- configurations are intended to be included within the ambit of this invention.

A related family of natural products is known as the milbemycins. The milbemycins have the same macrocyclic ring structure as the avermectins but have no substitution at position 13 and have a methyl or ethyl group at position 25 ($R_2$ =methyl or ethyl rather than isopropyl or sec-butyl as in the avermectins). The milbemycins and the fermentation conditions used to prepare them are described in U.S. Pat. No. 3,950,360. Closely related 13-deoxy-avermectin aglycones are prepared by chemical modification of the natural avermectins and have been described in U.S. Pat. Nos. 4,171,134 and 4,173,571.

Recently a number of related compounds have been described in European Patent Application EPO 170,006 and U.K. application 2,166,436 (see also Carter et al., *J. Antibiotics* 1988, 41, 519–529). These compounds are essentially 13-deoxy-avermectin aglycones in which the $R_2$ side chain contains a double bond and, in some cases, includes additional carbon atoms.

SUMMARY OF THE INVENTION

This invention is concerned with novel derivatives of avermectins in which a difluoro functionality has been introduced at the 4', 4", or 23 position and with novel derivatives of avermectin aglycones in which a difluoro functionality has been introduced at position 13 or 23. These derivatives are used as antiparasitic agents. The invention is also concerned with processes for the preparation of these compounds. The invention is also concerned with compositions for the treatment of parasitic diseases which contain one or more of the novel compounds of this invention as the active ingredient thereof.

DESCRIPTION OF THE INVENTION

The novel compounds of this invention are represented by structural formula:

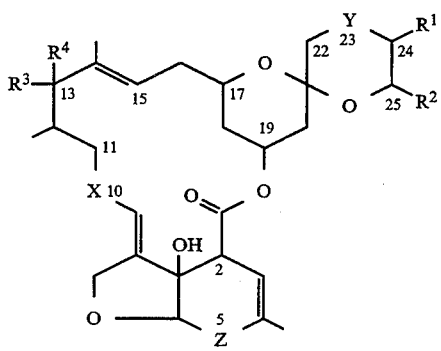

wherein:
Y is:
 (a) —$CH_2$—,
 (b) =CH—(22, 23 double bond),
 (c) —CH(OH)—,
 (d) —CO—,
 (e) —C(=NOH)—,
 (f) —C(=$NOCH_3$)—, or
 (g) —$CF_2$—;
$R^1$ is:
 (a) —H, or
 (b) —$CH_3$;
$R^2$ is:
 (a) —H,
 (b) —$C_1$–$C_8$ alkyl,
 (c) —$C_3$–$C_8$ cycloalkyl,
 (d) —$C_2$–$C_8$ alkenyl,
 (e) —$C_3$–$C_8$ cycloalkenyl, or
 (f) -aryl;
Z is:
 (a) —CH(OH)—,
 (b) —CO—,
 (c) —CH($OCH_3$)—,
 (d) —C(=NOH)—, or
 (e) —C(=$NOCH_3$)—;
$R^3$ is:
 (a) —H,
 (b) —F,
 (c) —($C_1$–$C_8$ alkoxy)$_n$ wherein n = 1, 2, or 3;

(d) 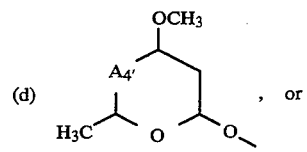 , or (e) 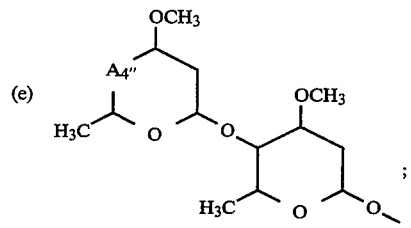 ;

Wherein:
A is:
 (a) —$CF_2$—,
 (b) —CH(OH),
 (c) —CHN$R^5R^{5A}$—,
 (d) —CHS$R^6$—,
$R^5$ and $R^{5A}$ are independently:
 (a) H,
 (b) $C^1$–$C^8$ alkyl,
 (c) $C^1$–$C^6$ alkenyl,
 (d) $C^1$–$C^6$ alkanoyl;
$R^6$ is:
 (a) $C^1$–$C^3$ alkoxyaminoalkyl,
 (b) $C^1$–$C^3$ alkylN$R^5R^{5A}$;
$R^4$ is:
 (a) —H, or
 (b) —F;
X is:
 (a) —$CH_2$—,
 (b) =CH—(10, 11 double bond),
 (c) —CH(OH)—,
 (d) —CHF—.

The term $C^1$–$C^8$ alkyl is intended to indicate those alkyl groups from 1 to 8 carbon atoms such as methyl, ethyl, propyl, isopropyl, pentyl, hexyl and the like, either straight or branched chain.

The term $C^2$–$C^8$ alkenyl is intended to include those alkenyl groups containing from 2 to 8 carbon atoms in either straight or branched chain which contains 1 or 2 carbon-carbon double bonds. Examples of such alkenyl groups include allyl, butenyl, pentadienyl, hexenyl, and the like.

In the instant invention the term "aryl" is intended to include aryl groups such as phenyl, 2-phenylpropene and the like.

The term "$C^1$–$C_8$ alkoxy" is intended to include those alkoxy groups from 1 to 8 carbon atoms in either a straight or branched chain. Examples of such alkoxy groups are methoxy, ethoxy, propoxy, isopropoxy, butoxy, sec-butoxy, pentoxy, hexoxy, heptoxy, and the like.

The term $C^1$–$C^6$ alkanoyl is intended to include those alkanoyl groups from 1 to 6 carbon atoms such as formyl, acetyl, propionyl, buytyryl, pentanoxyl, hexanoyl, and the like.

One preferred embodiment of the novel compounds of this invention is wherein:
$R^3$ is F;
$R^4$ is F;
Y is:
  (a) —CH$_2$—,
  (b) =CH— (22, 23 double bond),
  (c) —CH(OH)—,
  (d) —C(=NOCH$_3$), or
  (e) —CF$_2$;
$R^1$ is:
  (a) —H, or
  (b) —CH$_3$;
$R^2$ is:
  (a) —H,
  (b) sec-butyl, isopropyl, ethyl,
  (c) cyclohexyl, cyclopentyl,
  (d) 2-(4-methylpent-2-enyl), or
  (e) phenyl;
Z is:
  (a) —CH(OH)—, or
  (b) —C(=NOH)—;
X is:
  (a) —CH$_2$—,
  (b) =CH— (10, 11 double bond),
  (c) —CH(OH)—;

Most preferred compounds within this embodiment are realized when:
$R^3$ is F
$R^4$ is F
Y is:
  (a) —CH$_2$—,
  (b) =CH— (22, 23 double bond),
  (c) —CH(OH)—,
  (d) —C(NOCH$_3$);
$R^1$ is —CH$_3$;
$R^2$ is:
  (a) sec-butyl, or
  (b) isopropyl;
Z is :
  (a) —CH(OH)—,
  (b) —C(=NOH)—;
X is =CH— (10, 11 double bond).

Another preferred embodiment of the novel compounds of this invention is wherein:
Y is —CF$_2$—;
$R^1$ is:
  (a) —H, or
  (b) —CH$_3$;
$R^2$ is:
  (a) —H,
  (b) sec-butyl, isopropyl, ethyl,
  (c) cyclohexyl, cyclopentyl,
  (d) 2-(4-methylpent-2-enyl),
  (e) phenyl;
Z is :
  (a) —CH(OH)—,
  (b) —CH(OCH$_3$)—,
  (c) —C(=NOH)—, or
  (d) —C(=NOCH$_3$)—;
$R^3$ is:
  (a) —H,
  (b) —F,
  (c) OCH$_2$OCH$_3$,
  (d) OCH$_2$OCH$_2$CH$_2$OCH$_3$,

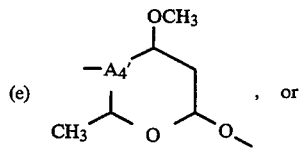

(e)

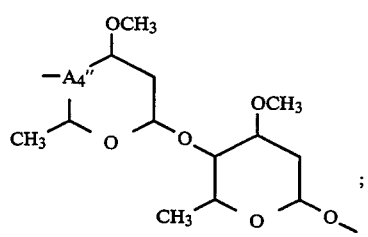

Wherein:
A is:
  (a) —CH(OH)—,
  (b) —CHNCH$_2$CH$_3$,
  (c) —CHSCH$_2$CH$_2$NOCCH$_3$,
  (d) —CF$_2$—;
$R^4$ is:
  (a) —H, or
  (b) —F;
X is:
  (a) —CH$_2$—,
  (b) =CH— (10, 11 double bond),
  (c) —CH(OH)—, or
  (d) —CHF—.

Most preferred compounds within this embodiment are realized when:
Y is —CF$_2$—;
$R^1$ is —CH$_3$—;
$R^2$ is:
  (a) sec-butyl, or
  (b) isopropyl;
Z is:
  (a) —CH(OH)—, or
  (b) —C(=NOH)—;
$R^3$ is:
  (a) H,
  (b) OCH$_2$OCH$_3$, or
  (c) OCH$_2$OCH$_2$CH$_2$OCH$_3$;
$R^4$ is —F—;
X is =CH— (10, 11 double bond).

Another preferred embodiment of the novel compounds of this invention is wherein:
$R^3$ is:

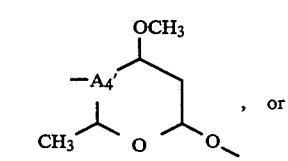

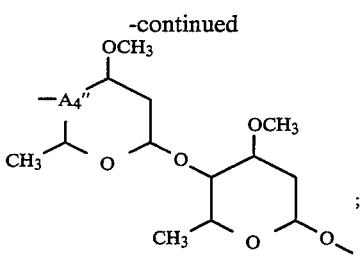

A is —CF$_2$—;
R$^4$ is —H;
Y is:
   (a) —CH$_2$—,
   (b) =CH—(22, 23 double bond),
   (c) —CH(OH)—,
   (d) —C(=NOH)—, or
   (e) —C(=NOCH$_3$),
   (f) —CF$_2$—;
R$^1$ is —CH$_3$;
R$^2$ is:
   (a) ethyl, isopropyl, sec-butyl,
   (b) cyclohexyl, cyclopentyl,
   (c) 2-(4-methylpent-2-enyl),
   (d) phenyl;
Z is:
   (a) —CH(OH)—,
   (b) —CO—,
   (c) —CH(OCH$_3$)—,
   (d) —C(NOH)—, or
   (e) —CNOCH$_3$—;
X is:
   (a) —CH$_2$—,
   (b) =CH—(10, 11 double bond),
   (c) —CH(OH)—, or
   (d) —CHF—.

Most preferred compounds within this embodiment are realized when:
R$^3$ is:

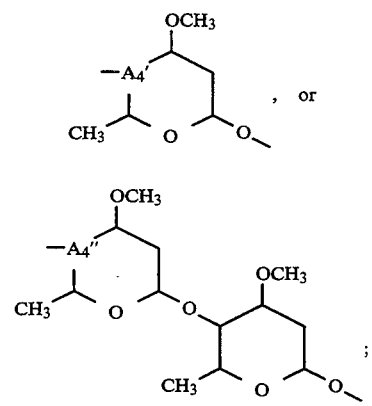

Wherein:
A is —CF$_2$—;
R$^4$ is —H;
Y is:
   (a) —CH$_2$—,
   (b) =CH—(22, 23 double bond),
   (c) —CH(OH)—,
   (d) —C(=NOCH$_3$);
R$^1$ is —CH$_3$;
R$^2$ is:
   (a) sec-butyl, or
   (b) isopropyl;
Z is:
   (a) —CH(OH)—,
   (b) —C(=NOH)—;
X is =CH—(10, 11 double bond).

Examples of the novel compounds of this invention are as follows:
4″-deoxy-4″-gem-difluoro-avermectin B1a;
4′-deoxy-4′-gem-difluoro-avermectin B1a monosaccharide;
13-deoxy-13-gem-difluoro-avermectin B1a/B1b aglycone;
23-gem-difluoro-ivermectin;
13-deoxy-13-gem-difluoro-ivermectin aglycone;
13-deoxy-13-gem-difluoro-22,23-dihydro-avermectin B1a/B1b aglycone;
13-gem-difluoro-13-deoxy-5-ketoxime-avermectin B1a and/or B1b aglycone;
23-gem-difluoro-4″-oxo-ivermectin;
23-gem-difluoro-4″-amino-ivermectin;
23-gem-difluoro-4″-acetylamino-ivermectin;
4″-acetylamino-23-gem-difluoro-ivermectin;
4″(2-acetylaminoethyl)thio-23-gem-difluoro-ivermectin
23-gem-difluoro-ivermectin aglycone;
13-deoxy-23-gem-difluoro-ivermectin aglycone;
23-gem-difluoro-ivermectin aglycone;
13-deoxy-13,23-bis-gem-difluoro-ivermectin aglycone;
23-gem-difluoro-10-fluoro-ivermectin;
13-deoxy-23-gem-difluoro-13-fluoro-ivermectin aglycone;
25-des(2-butyl)-25-methyl-13-deoxy-13-gem-difluoro-avermectin aglycone;
25-des(2-butyl)-25-cyclohexyl-13-deoxy-13-gem-difluoro-avermectin aglycone;
4″-deoxy-4″-gem-difluoro-5-deoxy-5-ketoxime-avermectin B1a/B1b;
23-gem-difluoro-5-deoxy-5-ketoxime-ivermectin;
10,11-dihydro-10-fluoro-13-deoxy-13-difluoro-avermectin B1a/B1b aglycone;

PREPARATION OF STARTING MATERIALS

The starting materials for this invention are disclosed in Albers-Schonberg et al., J. Am. Chem. Soc. 1981, 103, 4216–4221 and references cited therein (naturally occurring avermectins), Chabala et al., J. Med. Chem. 1980, 23, 1134–1136 (22,23-dihydro-avermectin B1(ivermectin), and 22,23-dihydro-avermectin B1-aglycone), Mrozik et al., J. Org. Chem. 1982, 47, 489–492 (avermectin aglycones), and U.K. application 2,166,436 (compounds with unsaturation in the R$_2$ side chain; see also Carter et al., J. Antibiotics 1988, 41, 519–529).

The novel compounds of this invention are prepared by the following procedures:
The hydroxyl group present at the 4′, 4″ or 23 position of the avermectin and at the 13 and 23 position of the avermectin aglycones can be converted to ketones and enones by a number of oxidation procedures, including oxidation with dimethylsulfoxide (DMSO) based systems commonly known to those skilled in the art as Swern (or Moffatt) oxidations (DMSO-oxalyl chloride, DMSO-acetic anhydride, DMSO-trifluoracetic anhydride and the like) as well as oxidations with chromioum based reagents (pyridinium chlorochromate, pyridinium dichromate, and the like) or other methods known to those skilled in the art. The DMSO based oxidation methods are preferred. These oxidations involve treating a solution of DMSO in a non-nucleophilic solvent such as dichloromethane, toluene, chloroform, ether, tetrahydrofuran and the like with an electrophilic activating agent such as oxalyl chloride (preferred), dicyclohexyl-carbodiimide (DCC), phosgene, and the like at temperatures ranging from −90° C. to −55° C. and stirring the mixture thus formed at this temperature for 10 to 60 minutes. To the oxidizing reagent thus generated is added, at the same temperature, a solution of the alcohol in the solvent used to generate to reagent. The solution is stirred at temperatures ranging from −90° C. to 55° C. for 10 to 90 minutes then a hindered base such as triethylamine, diisopropylethylamine, and the like is added. The temperature is raised from 0° C. to 30° C. and the mixture stirred at this temperature for 10 to 90 minutes. The reaction is then worked up and the product isolated and purified using standard techniques known to those skilled in the art.

During the oxidation procedure it is necessary to protect other secondary hydroxyl groups in the molecule with a protecting group which may be removed after the oxidation is accomplished. Suitable protecting groups include tert-butyldimethylsilyl, tert-butyldiphenylsilyl, trimethylsilyl, phenoxyacetyl, acetyl, and the like. The tert-butyldimethylsilyl group is preferred and is introduced by treating a solution of the alcohol in dimethylformamide (DMF) with an excess of imidazole and a silylating reagent such as tert-butyldimethyl-silylchloride, tert-butyldimethylsilyl-trifluoromethanesulfonate, and the like at temperatures ranging from 25° C. to 50° C. for 4 to 48 hours. The reaction is then worked up and the product isolated and purified using standard techniques known to those skilled in the art. Toluene and methylene chloride are the solvents of choice for these reactions. The protecting group may be removed by treatment with a solution of p-toluene-sulfonic acid (0.15–2%) in methanol at 0° C. to 25° C. for 0.5 to 8 hours. Alternatively, the protecting group may be removed by treatment with a solution of hydrogen fluoride in a pyridine/tetrahydrofuran solvent mixture. In both cases reaction workup and product isolation and purification are by standard techniques well known to those skilled in the art.

The ketones and enones at the various positions on the avermectin nucleus are converted directly into gem-difluorides by treatment with certain fluorinating agents in inert solvents. Diethylaminosulfur trifluoride is the reagent of choice, however, alternative fluorinating agents including sulfur tetrafluoride, morpholinosulfur trifluoride and molybdenum hexafluoride also are suitable. All hydroxyls in the molecule must be protected as above for the fluorination reaction to occur unless the conversion of an alcohol and a ketone to their respective mono- and difluorides in a single step is desired (note that it is not necessary to protect the tertiary hydroxyl present at position 7).

Oximes may be generated at position 5 via the 5-ketone. This ketone is prepared by oxidation of a compound with a 5-hydroxyl group using one of the oxidation methods described above. Oxidation with manganese dioxide is preferred. The oxidation is carried out by treating a solution of the alcohol in a non-hydroxylic solvent such as benzene, dichloromethane, chloroform, ethyl acetate, tetrahydrofuran, and the like with an excess of manganese dioxide at temperatures ranging from 25° C. to the reflux temperature of the solvent for 4 to 48 hours. The reaction is worked up and the product isolated and purified using standard techniques known to those skilled in the art. The ketone thus generated may be used to prepare oximes or alkoximes by a number of procedures. Generally, an excess of hydroxylamine hydrochloride (methoxylamine hydrochloride for a methoxime, etc.) is added to a solution of the ketone in pyridine and the solution stirred at temperatures ranging from 0° C. to 50° C. for 3–36 hours. Alternatively the amine hydrochloride is added to a solution of the ketone in a neutral solvent such as benzene, tetrahydrofuran, dioxane, dichloromethane, ethanol, and the like followed by a molar equivalent of a base such as sodium acetate, sodium hydroxide, triethylamine, and the like. The resulting mixture is stirred at temperatures ranging from 0° C. to 50° C. for 3–36 hours. In either case the reaction is worked up and the product is isolated and purified using standard techniques known to those skilled in the art.

In the instances where the ultimate precursor is a milbemycin-type compound (lacks substitution at position 13) it is necessary to introduce a hydroxyl group at position 13. This may be accomplished by allylic oxidation of the C-14–15 olefin with selenium dioxide. The oxidation is effected by adding an excess of selenium dioxide to a solution of the olefin in a solvent such as ethanol, methanol formic acid, and the like. The mixture is stirred at temperatures ranging from 25° C. to reflux for 3–36 hours. The reaction is worked up and the product isolated and purified using standard techniques known to those skilled in the art. The resulting 13-hydroxy-analog is then oxidized to the 13-ketone using one of the oxidation procedures outlined above. Note that the stereochemistry of the hydroxyl group at position 13 is unimportant since this stereochemistry is lost in the conversion of the alcohol to the ketone.

The instant compounds of this invention are unexpectedly potent antiparasitic agents against endo and ecto parasites, particularly helminths and arthropods, which cause numerous parasitic diseases in humans, animals, and plants.

Parasitic diseases may be caused by either endoparasites or ectoparasites. Endoparasites are those parasites which live inside the body of the host, either within an organ (such as the stomach, lungs, heart, intestines, etc.) or simply under the skin. Ectoparasites are those parasites which live on the outer surface of the host but still draw nutrients from the host.

The endoparasitic diseases generally referred to as helminthiasis are due to infection of the host with parasitic worms known as helminths. Helminthiasis is a prevalent and serious worldwide economic problem due to infection of domesticated animals such as swine, sheep, horses, cattle, goats, dogs, cats, and poultry. Many of these infections are caused by the group of worms described as nematodes which cause diseases in various species of animals throughout the world. These diseases are frequently serious and can result in the death of the infected animal. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris, and Parascaris. Many parasites are species specific (infect only one host) and most also have a preferred site of infection within the animal. Thus Haemonthus and Ostertagia primarily infect the stomach while Nematodirus and Cooperia mostly attack the intestines. Other parasites prefer to reside in the heart, eyes, lungs, blood vessels, and the like while still others are subcutaneous parasites. Helminthiasis can lead to weakness, weight loss, anemia, intestinal damage, malnutrition, and damage to other organs. If left untreated these diseases can result in the death of the animal.

Infections by ectoparasitic arthropods such as ticks, mites, lice, stable flies, hornflies, blowflies, fleas, and the like are also a serious problem. Infection by these parasites results in loss of blood, skin lesions, and can interfere with normal eating habits thus causing weight loss. These infections can also result in transmission of serious diseases such as encephalitis, anaplasmosis, swine pox, and the like which can be fatal.

Animals may be infected by several species of parasite at the same time since infection by one parasite may weaken the animal and make it more susceptible to infection by a second species of parasite. Thus a compound with a broad spectrum of activity is particularly advantageous in the treatment of these diseases. The compounds of this invention have unexpectedly high activity against these parasites, and in addition are also active against Dirofilaria in dogs, Nematospiroides and Syphacia in rodents, biting insects, and migrating diperous larvae such as Hypoderma sp. in cattle, and Gastrophilus in horses.

The instant compounds are also useful against endo and ecto parasites which cause parasitic diseases in humans. Examples of such endoparasites which infect man include gastro-intestinal parasites of the genera Ancylostoma, Necator, Ascaris, Strongyloides, Trichinella, Capillaria, Trichuris, Enterobius, and the like. Other endoparasites which infect man are found in the blood or in other organs. Examples of such parasites are the filarial worms Wucheria, Brugia, Onchocerca, and the like as well as extra-intestinal stages of the intestinal worms Strongylides and Trichinella. Ectoparasites which parasitize man include arthropods such as ticks, fleas, mites, lice, and the like and, as with domestic animals, infections by these parasites can result in transmission of serious and even fatal diseases. The instant compounds are active against these endo and ecto parasites and in addition are also active against biting insects and other dipterous pests which annoy humans.

The instant compounds are also useful against common household pests such as Blatella sp. (cockroach), Tineola sp. (clothes moth), Attagenus sp. (carpet beetle), *Musca domestica* (housefly) and against *Solenopsis invicta* (imported fire ant).

The compounds are furthermore useful against agricultural pests such as aphids (Acyrthiosiphon sp.), locusts, and boll weevils as well as against insect pests which attack stored grains such as Tribolium sp. and against immature stages of insects living on plant tissue. The compounds are also useful as a nematodicide for the control of soil nematodes which may be agriculturally important.

For use as an antiparasitic agent in animals the instant compounds may be administered internally either orally or by injection, or topically as a liquid drench or as a shampoo.

For oral administration, the compounds may be administered in capsule, tablet, or bolus form or alternatively they can be mixed in the animals feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, and/or binders such that a uniform mixture is obtained. An inert ingredient is one that will not react with the instant compounds and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5% by weight of the active ingredient.

The compounds may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the instant compounds is possible through the use of a liquid drench or a shampoo containing the instant compounds as an aqueous solution or suspension. These formulations generally contain a suspending agent such as bentonite and normally will also contain an antifoaming agent. Formulations containing from 0.005 to 10% by weight of the active ingredient are acceptable. Preferred formulations are those containing from 0.01 to 5% by weight of the instant compounds.

The instant compounds are primarily useful as antiparasitic agents for the treatment and/or prevention of helminthiasis in domestic animals such as cattle, sheep, horses, dogs, cats, goats, swine, and poultry. They are also useful in the prevention and treatment of parasitic infections of these animals by ectoparasites such as ticks, mites, lice, fleas and the like. They are also effective in the treatment of parasitic infections of humans. In treating such infections the compounds of this invention may be used individually or in combination with each other or with other unrelated antiparasitic agents. The dosage of the instant compounds required for best results depends on several factors such as the species and size of the animal, the type and severity of the infection, the method of administration and the compound used. Oral administration of the instant compounds at a dose level of from 0.0005 to 10 mg per kg of animal body weight, either in a single dose or in several doses spaced a few days apart, generally gives good results. A single dose of one of the instant compounds normally gives excellent control however repeat doses may be given to combat re-infection or for parasite species which are unusually persistent. The techniques for administering these compounds to animals are known to those skilled in the veterinary field.

The compounds of this invention may also be used to combat agricultural pests which attack crops either in the field or in storage. The compounds are applied for such uses as sprays, dusts, emulsions and the like either to the growing plants or the harvested crops. The techniques for applying these compounds in this manner are known to those skilled in the agricultural arts.

The following examples are provided in order that this invention might be more fully understood; they are not to be construed as limitative of the invention. The avermectin derivatives prepared in the following examples are generally isolated as amorphous solids rather than crystalline solids. They are characterized analytically using techniques such as nuclear magnetic resonance, mass spectrometry, and the like. Being amorphous the compounds are not characterized by sharp melting points but the chromatographic and analytical methods employed indicate that they are pure.

EXAMPLE 1

5-O-tert-butyldimethylsilyl-4"-oxo-avermectin B1a (1)

Two grams of Avermectin B1a was dissolved in 10 mL THF at RT to which was added 750 mg tert-butyldimethylsilyl chloride and 680 mg imidazole. The reaction was stirred for 6 hrs at RT then poured into 30 mL saturated $NaHCO_3$. The solution was extracted with EtOAc, dried ($MgSO_4$), filtered and concentrated under reduced pressure. Pure 5-O-tert-butyldimethylsilyl-avermectin B1a (1.82 g, 81%) was obtained as a white solid by flash chromatography on silica gel using 6:4 hexanes:EtOAc as eluant. 5-O-tert-butyldimethylsilyl-avermectin B1a (1.5g) was dissolved in 8 mL isopropyl acetate at −30° C. to which was added, sequentially, 431 mL dimethylsulfoxide, 1.07 mL triethylamine and 452 mL $(PhO)P(O)Cl_2$. After 15 min at −30° C., the solution was warmed to 0° C. and stirred for 30 min. The reaction was purified without workup by flash chromatography on silica gel using 7:3 hexanes:EtOAc as eluant to yield pure 5-O-tert-butyldimethylsilyl-4"-oxo-avermectin B1a (1.36 g, 91) as a white powder.

EXAMPLE 2

5-O-tert-butyldimethylsiyl-4"-oxo-7-O-trimethylsilyl-avermectin B1a (2)

One gram of 5-O-tert-butyldimethylsilyl4"-oxo-avermectin B1a (1) was dissolved in 3 mL dimethylformamide to which was added 2 mL bis(trimethylsilyl)trifluoroacetamide. The reaction was stirred at RT for 12 hours and then purified without workup by flash chromatography on silica gel using 85:15 hexanes:EtOAc as eluant to yield pure 5-O-tert-butyldimethylsilyl-4"-oxo-7-O-trimethylsilyl-avermectin B1a (793 mg, 74%) as a white powder.

EXAMPLE 3

4"-deoxy-4"-gem-difluoro-5-O-tert-butyldimethylsilsyl-7-O-trimethylsilyl-avermectin B1a (3)

Compound 5-O-tert-butyldimethylsilyl-4"-oxo7-O-trimethylsilyl-avermectin B1a above (50mg) was dissolved in 1 mL toluene at 0° C. to which was added 150 uL diethylaminosulfur trifluoride. The solution was warmed to RT and stirred for 10 hrs. The reaction was quenched by its dropwise addition to an ice-cold solution of saturated $NaHCO_3$. The solution was extracted with EtOAc and dried ($MgSO_4$). The solution was filtered, concentrated under reduced pressure and purified by flash chromatography on silica gel to yield 27 mg 4"-deoxy-4"-gem-difluoro-5-O-tert-butyldimethylsilyl-7-O-trimethylsilyl-avermectin B1a (53%) as a pale yellow powder. This compound can also be prepared as above using methylene chloride in place of toluene and EtOAc. The solution is purified by flash chromatography on silica gel using 85:15 hexanes:EtOAc to yield 24 mg of 4"-deoxy-4"-gem-difluoro-5-O-tert-butyldimethylsilyl-7-O-trimethylsily l-avermectin B1a (47%) as a pale yellow powder.

EXAMPLE 4

4"-deoxy-4"-gem-difluoro-avermectin B1a (4)

Compound 4"-deoxy-4"gem-difluoro-5-O-tert-butyldimethylsilyl-7-O-trimethylsilyl-avermectin B1a above, (55 mg) was dissolved in 3 mL THF at RT to which was added 1 mL HF.pyridine solution (25 g HF.pyridine, 10 mL pyridine, 25 mL THF) and stirred for 48 hrs. The solution was poured into 20 mL 1:1 water:$Et_2O$ and the layers separated. Each layer was neutralized separately, the aqueous layer was extracted with $Et_2O$, the organic layers combined and dried ($MgSO_4$). The solution was filtered and concentrated under reduced pressure. Pure 4"-deoxy-4"-gem-difluoro-avermectin B1a (30 mg, 66%) was obtained after flash chromatography on silica gel using 3:2 hexanes:EtOAc as eluant.

EXAMPLE 5

5-O-tert-butyldimethylsilyl-4'-oxo-avermectin B1a monosaccharide (5)

Avermectin $B_{1a}$ monosaccharide (1.0 g) was dissolved in 8 mL THF at RT to which was added 455 mg tert-butyldimethylsilyl chloride followed by 410 mg imidazole. The reaction was stirred at RT for 6 hrs and then poured into 30 mL saturated $NaHCO_3$. The solution was extracted with EtOAc and dried ($MgSO_4$). The solution was filtered and concentrated under reduced pressure. Pure 5-O-tert-butyldimethylsilyl-avermectin B1a monosaccharide (933 mg, 81%) was obtained as a white powder following flash chromatography on silica gel using 6:4 hexanes:EtOAc as eluant. The monosaccharide (980 mg) was dissolved in 6 mL isopropyl acetate at −30° C. to which was added, sequentially, 330 uL dimethyl sulfoxide, 817 uL triethylamine and 347 uL (PhO )$P(O)Cl_2$. The solution was stirred at −20° C. for 15 min, then warmed to 0° C. for 20 min. The solution was purified without workup by flash chromatography on silica gel using 8:2 hexanes:EtOAc as eluant to yield pure 5-O-tert-butyldimethylsilyl-4'-oxo-avermectin B1a monosaccharide (862 mg, 88%) as a white powder.

EXAMPLE 6

5-O-tert-butyldimethylsilyl-4'-deoxy-4'-gem-difluoro-7-O-trimethylsilyl-avermectin B1a monosaccharide (6)

Pure 5-O-tert-butyldimethylsilyl-4'-oxo-avermectin B1a monosaccharide (1.5 g) was dissolved in 4 mL dimethylformamide to which was added 3 mL bis(-trimethylsilyl)-trifluoroacetamide. The reaction was stirred at RT for 12 hours and then purified without workup by flash chromatography on silica gel using 80:20 hexanes:EtOAc as eluant to yield pure ketone, 5-O-tert-butyldimethylsilyl-4'-oxo-7-O-trimethylsilyl-avermectin monosaccharide (1.28 g, 79%) as a white powder. Place 300 mg of the ketone in 2 mL toluene at 0° C. and to this add 300 mL diethylaminosulfur trifluoride. Warm the reaction to RT and stir for 10 hrs. Quench the reaction by dropwise addition to an ice-cold solution of 10 mL saturated NaHCO$_3$, extract with EtOAc and dry (MgSO$_4$). Filter and concentrate the solution under reduced pressure. Pure 5-O-tert-butyldimethylsilyl-4'-deoxy-4'-gem-difluoro-7-O-trimethylsilyl-avermectin B1a monosaccharide may be obtained by flash chromatography on silica gel.

EXAMPLE 7

4'-deoxy-4'-gem-difluoro-avermectin B1a monosaccharide (7)

Dissolve 100 mg 5-O-tert-butyldimethylsilyl4'-deoxy-4'-gem-difluoro-7-O-trimethylsilyl-avermectin B1a monosaccharide in 3 mL THF at RT, add 1 mL HF.pyridine solution (25 g HF.pyridine, 10 mL pyridine, 25 mL THF) and stir for 48 hrs. Pour the solution into 20 mL 1:1 water:Et$_2$O and separate the layers. Neutralize each layer separately with saturated NaHCO$_3$, extract the aqueous layer with Et$_2$O, combine and dry the organic layers (MgSO$_4$). Filter the solution and concentrate it under reduced pressure. Pure 4'-deoxy-4'-gem-difluoro-avermectin B1a monosaccharide may be obtained after flash chromatography on silica gel.

EXAMPLE 8

5-O-tert-butyldimethylsilyl-7-O-trimethylsilyl-avermectin B1a aglycone (8)

Avermectin B$_{1a}$ aglycone (1.0 g) was dissolved in 8 mL THF at RT to which was added 595 mg tert-butyldimethylsilyl chloride and 510 mg imidazole. After 4 hrs at RT, the solution was poured into 30 mL saturated NaHCO$_3$, extracted with EtOAc and dried (MgSO$_4$). The solution was filtered and concentrated under reduced pressure. Pure 5-O-tert-butyldimethylsilyl-avermectin B1a aglycone (1.03 g, 87%) was obtained by flash chromatography on silica gel using 8:2 hexanes:EtOAc as eluant. This agylcone (1.03 g) was dissolved in 3 mL DMF at RT to which was added 2 mL bis(-trimethylsilyl)trifluoroacetamide. The reaction was stirred overnight at RT and then purified without workup by flash chromatography on silica gel using 85:15 hexanes:EtOAc as eluant. The resultant 5-O-tert-butyldimethylsilyl-7,13-bis-trimethylsilyl-avermectin aglycone was concentrated under reduced pressure and then dissolved in 10 mL methanol at RT. To this was added 5 mg pyridinium p-toluenesulfonate and the reaction stirred for 20 min. The solution was then poured into 50 mL saturated NaHCO$_3$, extracted with methylene chloride and dried (MgSO$_4$)Pure 5-O-tert-butyldimethylsilyl-7-O-trimethylsilyl-avermectin B1a aglycone (939 mg, 83%) of a white powder is obtained.

EXAMPLE 9

5-O-tert-butyldimethylsilyl-7-O-trimethylsily-13-deoxy-13-gem-difluoro-avermectin aglycone (9)

Pure 5-O-tert-butyldimethylsilyl-7-O-trimethylsilyl-avermectin B1a aglycone (475 mg) was dissolved in 3 mL methylene chloride at RT to which was added 287 mg Dess-Martin reagent. After 10 min, the reaction was purified without workup by flash chromatography on silica gel using 9:1 hexanes:acetone as eluant to yield pure enone, 5-O-tert-butyldimethylsilyl-7-O-trimethylsilyl-13-oxo-ivermectin aglycone (469 mg, 98) as a white powder. The enone (350 mg) was placed in 2 mL freshly distilled toluene to which was added 1 mL diethylaminosulfur trifluoride. The solution was then deated to 55° C. for four hrs. The reaction was quenched by adding it dropwise to an ice-cold saturated $NaHCO_3$ solution. This was then extracted with EtOAc and dried ($MgSO_4$). The solution was filtered and concentrated under reduced pressure. Preliminary purification was accomplished by flash chromatography on silica gel using 9:1 hexanes:acetone as eluant. Further purification by preparative reversed phase HPLC (Waters C-18 column, 2.5×30 cm) using 91.3:8.7 MeOH:-water (v:v) yield 65 mg 5-O-tert-butyldimethylsilyl-7-O-trimethylsilyl-13-deoxy-13-gem-difluoro-avermectin aglycone (18%).

EXAMPLE 10

5-O-tert-butyldimethylsilyl-7-O-trimethylsilyl-13-deoxy-13-difluoro-10,11-dihydro-10-hydroxy-avermectin B1a/B1b aglycone (10)

Place 100 mg 5-O-tert-butyldimethylsilyl-7-O-trimethylsilyl-13-deoxy-13-difluoro-avermectin B1a/B1b aglycone in 3 mL of acetone containing 0.3 mL water at RT and to this add 25 mg N-bromoacetamide in one portion. Stir the solution for 1 hr in the dark and work up by extraction with $Et_2O$. Dry ($MgSO_4$), filter and concentrate the solution under reduced pressure. Purify the product (5-O-tert-butyldimethylsilyl-7-O-trimethylsilyl-11-bromo-10-hydroxy-13-deoxy-13-difluoro-avermectin B1a/B1b aglycone) by flash chromatography on silica gel. Dissolve the bromide thus purified in 3 mL toluene and add 1 mL tri-n-butyl tin hydride. Heat this solution to 100° C. for 1 hr. Pure 5-O-tert-butyldimethylsilyl-7-O-trimethylsilyl-13-deoxy-13-difluoro-10,11-dihydro-10-hydroxy-avermectin B1a/B1b aglycone may be obtained by flash chromatography on silica gel.

EXAMPLE 11

5-O-tert-butyldimethylsilyl-7-O-trimethylsilyl-10,11-dihydro-10-fluoro-13-deoxy-13-difluoro-avermectin B1a/B1b aglycone (11)

Place 100 mg 5-O-tert-butyldimethylsilyl-7-O-trimethylsilyl-13-deoxy-13-difluoro-10,11-dihydro-10-hydroxy-avermectin B1a/B1b aglycone in 3 mL methylene chloride at −78° C. and add 0.1 mL diethylaminosulfur trifluoride. After 1 hr at −78° C., quench the reaction with 5 mL 7% aqueous $Na_2CO_3$ solution. Extract the product with methylene chloride, dry ($MgSO_4$), filter and concentrate under reduced pressure. Pure 5-O-tert-butyldimethylsilyl-7-O-trimethylsilyl-10,11-dihydro-10-fluoro-13-deoxy-13-di fluoro-avermectin B1a/B1b aglycone may be obtained following flash chromatography on silica gel.

EXAMPLE 12

10.11-dihydro-10-fluoro-13-deoxy-13-difluoro-avermectin B1a/B1b aglycone (12)

Place 50 mg 5-O-tert-butyldimethylsilyl-7-O-trimethylsilyl-10,11-dihydro-10-fluoro-13-deoxy-13-difluoro-avermectin B1a/B1b aglycone in 4 mL THF at RT and add to this 1 mL HF.pyridine solution (25 g HF.pyridine, 10 mL pyridine, 25 mL THF) and stir for 24 hrs.

Pour the solution into 20 mL 1:1 water:Et$_2$O and separate the layers. Neutralize each layer with saturated NaHCO$_3$, and extract the aqueous layer with Et$_2$O. Dry the combined organic layers (MgSO$_4$), filter and concentrate under reduced pressure. Pure 10,11-dihydro-10-fluoro-13-deoxy-13-difluoro-avermectin B1a/B1b aglycone may be obtained following flash chromatography on silica gel.

EXAMPLE 13

13-deoxy-13-gem-difluoro-avermectin B1a/B1b aglycone (13)

5-O-tert-butyldimethylsilyl-7-O-trimethylsilyl-13-deoxy-13-gem-difluoro-avermectin aglycone (65 mg) was dissolved in 4 mL THF at RT to which was added 1 mL HF.pyridine solution (25 g HF.pyridine, 10 mL pyridine, 25 mL THF) and stirred for 48 hrs. The solution was poured into 30 mL 1:1 water:Et$_2$O and the layers separated. Each layer was neutralized separately, the aqueous layer was extracted with Et$_2$O, the organic layers combined and dried (MgSO$_4$). The solution was filtered and concentrated under reduced pressure. Pure 13-deoxy-13-gem-difluoro-avermectin aglycone (28 mg, 54%) was obtained after flash chromatography on silica gel using 1:1 hexanes:EtOAc as eluant.

EXAMPLE 14

13-gem-difluoro-5-ketoxime-avermectin B1a and/or B1b aglycone (14)

Place 100 mg 13-deoxy-13-gem-difluoro-avermectin aglycone in 4 mL EtOAc at RT and add to it 200 mg freshly prepared MnO$_2$. Stir the solution for 30 min and then filter the solution through a bed of Celite using EtOAc as eluant and then concentrate the solution under reduced pressure. Dissolve the 5-keto compound thus formed in 4 mL EtOAc and add 150 uL 1.0M zinc chloride in ether followed by 100 uL TMSONH$_2$(905 umol). Stir for 2 hrs at RT, add 1 ml saturated NaHCO$_3$ and stir for 15 additional min. Dilute the solution with 4 mL water, extract with EtOAc and dry (MgSO$_4$). Filter the solution and concentrate under reduced pressure. Pure 13-gem-difluoro-5-ketoxime-avermectin B1a and/or B1b aglycone may be obtained following flash chromatography on silica gel.

Pure 4"-deoxy-4"-gem-difluoro-5-deoxy-5-ketoxime-avermectin B1a/B1b and pure 23-gem-difluoro-5-deoxy-5-ketoxime-ivermectin can be obtained through a similar process except that the starting materials (200 mg) are 4"-deoxy-4"-gem-difluoro-avermectin B1a/B1b and 23-gem-difluoro-ivermectin, respectively.

EXAMPLE 15

4",5-bis-O-tert-butyldimethylsilyl-avermectin B2a (15)

To a solution of 58.2 g avermectin B2a in 400 mL sieve-dried dimethylformamide and 30 mL freshly distilled triethylamine was added a solution of 29.8 g tert-dimethylsilyl chloride (198 mmol) in 200 mL methylene chloride. The mixture was stirred at RT for 16 hrs then poured into ice water and extracted with methylene chloride. The organic phases were combined and washed with water, brine and dried over MgSO$_4$. Evaporation of the solvent afforded an oil which was purified by silica gel liquid chromatography using 2:8 EtOAc:hexanes as eluant to yield 4",5-bis-O-tert-butyldimethylsilyl-avermectin B2a (34.2 g, 47%)

EXAMPLE 16

4",5-bis-O-tert-butyldimethylsilyl-23-oxo-ivermectin (16)

Methylene chloride (400 ml) and 16 mL oxalyl chloride (185 mmol) were contacted and cooled to −78° C., under nitrogen, while a solution of 25 mL dimethylsulfoxide (350 mmol) in 200 mL methylene chloride was added dropwise over 30 min keeping the internal temperature below −65° C. The mixture was stirred at −70° C. for 1 hr. A solution of 4",5-bis-O-tert-butyl-dimethylsilyl-avermectin B2a, 114.75 g, (103 mmol) in 900 mL methylene chloride was then added dropwise over 45 min while keeping the internal temperature below −65° C. After an additional 2 hrs at −70° C., 115 mL triethylamine was added dropwise over 10 min again keeping the temperature below −65° C. The reaction was then stirred at approximately 10° C. for 1 hr before the solvent was removed in vacuo. The residue was taken up in 1.5 L Et$_2$O and washed with 500 mL water. The aqueous layer was extracted with 500 mL Et$_2$O. The combined ether layers were washed sequentially with 2×1 L water, 1 L saturated NaHCO$_3$, 1 L brine and dried (MgSO$_4$). The solution was filtered and the solvent removed under reduced pressure to afford 100 g yellow foam which was purified by column chromatography (4 kg silica gel, 5–25% EtOAc in hexanes as eluant. Pure 4",5-bis-O-tert-butyldimethylsilyl-23-oxo-ivermectin (101 g, 88%) was thus obtained as a pale yellow foam.

EXAMPLE 17

4",5-bis-O-tert-butyldimethylsilyl-7-O-trimethylsilyl-23-oxo-ivermectin

To a solution of 5 g of 4",5-bis-O-tert-butyldimethylsilyl-23-oxo-ivermectin in 5 mL dimethylformamide at RT was added 5 mL bis(trimethylsilyl)trifluoroacetamide. The solution was stirred at RT for 12 hrs then purified without workup by flash chromatography on silica gel using 9:1 hexanes:EtOAc as eluant to yield pure 4",5-bis-O-tert-butyldimethylsilyl-7-O-trimethylsilyl-23-oxo-ivermectin (3.03 g, 57%) as a pale yellow foam.

EXAMPLE 18

4",5-bis-O-tert-butyldimethylsilyl-7-O-trimethylsilyl-23-gem-difluoro-ivermectin (18)

Pure 4",5-bis-O-tert-butyldimethylsilyl-7-O-trimethylsilyl-23-oxo-ivermectin (300 mg) was dissolved in 3 mL methylene chloride in a four dram vial at 0° C. To this was added 400 uL diethylamino-sulfur trifluoride. The cooling bath was removed, the reaction stirred at RT for 1 hr and then was heated to 35° C. for 12 hr. The reaction was quenched by dropwise addition to an ice-cold solution of saturated NaHCO$_3$, extracted with EtOAc and dried (MgSO$_4$). The solution was filtered and concentrated under reduced pressure. Pure 4",5-bis-O-tert-butyldimethylsilyl-7-O-trimethylsilyl-23-gem-difluoro-ivermectin (121 mg, 40%) was obtained after flash chromatography on silica gel using 85:15 hexanes:EtOAc as eluant.

EXAMPLE 19

23-gem-difluoro-ivermectin (19)

Pure 4",5-bis-O-tert-butyldimethylsilyl-7-O-trimethylsilyl-23-gem-difluoro-ivermectin (85 mg) was dissolved in 4 mL THF at RT to which was added 1 mL HF.pyridine solution (25 g HF.pyridine, 10 mL pyridine, 25 mL THF) and stirred for 48 hrs. The solution was poured into 30 mL 1:1 water:Et$_2$O and the layers separated. Each layer was neutralized separately, the aqueous layer was extracted with Et$_2$O, the organic layers combined and dried (MgSO$_4$). The solution was filtered and concentrated under reduced pressure. Pure 23-gem-difluoro-ivermectin (51 mg, 81%) was obtained after flash chromatography on silica gel using 3:2 hexanes:EtOAc as eluant.

EXAMPLE 20

5-tert-butyldimethylsilyl-23-gem-difluoro-ivermectin (20)

Place 200 mg of 23-gem-difluoro-ivermectin in 3 mL dimethylformamide at RT and add to it 66 mg imidazole and 73 mg tert-butyldimethylsilyl chloride. Stir for 2 hrs and then pour into water, extract with EtOAc and dry (MgSO$_4$). Filter and concentrate the solution under reduced pressure. Pure 5-tert-butyldimethylsilyl-23-gem-difluoro-ivermectin may be obtained following flash chromatography on silica gel.

EXAMPLE 21

5-tert-butyldimethysilyl-23-gem-difluoro-4"-oxo-22,23-dihydro-ivermectin (21)

Place 100 mg of 5-tert-butyldimethylsilyl- 23-gem-difluoro-ivermectin in 3 mL isopropyl acetate at −30° C. To this solution, add, sequentially, 56 uL diisopropylethylamine (312 umol), 22 uL methyl sulfoxide (312 umol) and 44 uL phenylphosphonic dichloride (312 umol). Warm this solution slowly to RT over 1 hr. Quench the reaction with 1 mL saturated NaHCO$_3$, extract with methylene chloride and dry (MgSO$_4$). Filter the solution and concentrate under reduced pressure. Pure 5-tert-butyldimethylsilyl-23-gem-difluoro-4"-oxo-ivermectin may be obtained following flash chromatography on silica gel.

EXAMPLE 22

5-tert-butyldimethylsilyl-23-gem-difluoro-4"-amino-4"-deoxy-ivermectin (22)

Place 100 mg of 5-tert-butyldimethylsilyl-23-gem-difluoro-4"-oxo-ivermectin, in 3 mL methanol with 160 mg ammonium acetate and to this is added 12 mg sodium cyanoborohydride. Stir the reaction at RT for 1 hr and then pour the solution into saturated NaHCO$_3$. The organic products are extracted with EtOAc and dried (MgSO$_4$). Filter and concentrate the solution under reduced pressure. Pure 5-tert-butyldimethylsilyl-23-gem-difluoro-4"-amino-ivermectin may be obtained following flash chromatography on silica gel using 97:3 methylene chloride:methanol as eluant.

EXAMPLE 23

5-tert-butyldimethylsilyl-23-gem-difluoro-4"-acetylamino-ivermectin (23)

Dissolve 50 mg of 5-tert-butyldimethylsilyl-23-gem-difluoro-4"-amino-ivermectin, in 2 mL methylene chloride at 0° C. and add 200 uL pyridine, 25 mg 4-dimethylaminopyridine and 100 uL acetic anhydride. After 3 hrs at 0° C., pure 5-tert-butyldimethylsilyl-23-gem-difluoro-4"-acetylamino-ivermectin may be obtained without workup by direct flash chromatography on silica gel.

EXAMPLE 24

4"-acetylamino-23-gem-difluoro-ivermectin (24)

Place 25 mg of 5-tert-butyldimethylsilyl-23-gem-difluoro-4"-acetylamino-ivermectin in 3 mL THF at RT and add 1 mL HF.pyridine solution (25 g HF.pyridine, 10 mL pyridine, 25 mL THF) and stir for 12 hrs. Pour the solution into 20 mL 1:1 water:Et$_2$O and separate the layers. Neutralize each layer separately with saturate NaHCO$_3$ and extract the aqueous layer with Et$_2$O. Dry (MgSO$_4$) the combined organic layers. Filter the solution and concentrate it under reduced pressure. Pure 4"-acetylamino-23-gem-difluoro-ivermectin may be obtained after flash chromatography on silica gel.

EXAMPLE 25

5-tert-butyldimethylsilyl-4"(2-acetylaminoethyl)thio-23-gem-difluoro-ivermectin (25)

Place 100 mg of 5-tert-butyldimethylsilyl-23-gem-difluoro-ivermectin in 4 mL methylene chloride at 0° C. and add to it 75 uL diisopropylethylamine and 50 mg 4-dimethylamino- pyridine. Add 65 uL trifluormethanesulfonic anhydride dropwise and stir for 1 hr. Filter the solution without workup through a 4 cm bed of silica gel using 1:1 hexanes:EtOAc as eluant and concentrate the resulting solution to a foam. Dissolve the trifluoromethanesulfonate thus formed 3 mL dimethylformamide at RT and add 100 mg 2-(acetyl- amino)ethyl mercaptan, 10 mg 18-crown-6 and 100 mg anhydrous potassium carbonate. Stir the solution for 1 hr and then pour it into water. Extract with EtOAc, dry (MgSO$_4$), filter and concentrate the solution under reduced pressure. Pure 5-tert- butyldimethylsilyl-4"(2-acetylaminoethyl)thio-23-gem-difluoro-ivermectin may be obtained following flash chromatography on silica gel.

EXAMPLE 26

4"-(2-acetylaminoethyl)thio-23-gem-difluoro-ivermectin (26)

Place 25 mg of 5-tert-butyldimethylsilyl-4"(2-acetylaminoethyl)thio-23-gem-difluoro-ivermectin, in 3 mL THF at RT and add 1 mL HF.pyridine solution (25 g HF.pyridine, 10 mL pyridine, 25 mL THF) and stir for 12 hrs. Pour the solution into 20 mL 1:1 water:Et$_2$O and separate the layers. Neutralize each layer separately with saturate NaHCO$_3$ ; and extract the aqueous layer with Et$_2$O. Dry (MgSO$_4$) the combined organic layers. Filter the solution and concentrate it under reduced pressure. Pure 4"-(2-acetylaminoethyl)thio-23-gem-difluoro-ivermectin may be obtained after flash chromatography on silica gel.

EXAMPLE 27

23-gem-difluoro-ivermectin aglycone (27)

Add 100 mg of 23-gem-difluoro-ivermectin, to a 1% solution of sulfuric acid in 3 mL methanol at RT and stir the solution for 12 hrs. Pour the solution into saturated ice-cold NaHCO$_3$, extract with EtOAc and dry (MgSO$_4$). Filter and concentrate the solution under reduced pressure. Pure 23-gem-difluoro-ivermectin aglycone may be obtained following flash chromatography on silica gel.

EXAMPLE 28

5-tert-butyldimethylsilyl-23-gem-difluoro-ivermectin aglycone (28)

Dissolve 50 mg of 23-gem-difluoro-ivermectin aglycone, in 2 mL dimethylformamide at RT and add 25 mg imidazole and 27 mg tert-butyldimethylsilyl chloride. Stir the solution for 1 hr and then pour it into water. Extract with EtOAc, dry (MgSO$_4$), filter and concentrate the solution under reduced pressure. Pure 5-tert-butyldimethylsilyl-23-gem-difluoro-ivermectin aglycone may be obtained following flash chromatography on silica gel.

EXAMPLE 29

5-tert-butyldimethylsilyl-13-deoxy-23-gem-difluoro-ivermectin aglycone (29)

Dissolve 25 mg of 5-tert-butyldimethylsilyl-23-gem-difluoro-ivermectin B1a and/or B1b aglycone, in 1 mL methylene chloride at RT and add 150 uL diisopropylethylamine, 20 mg 4-dimethylaminopyridine and 160 mg ortho-nitrobenzenesulfonyl chloride. Stir for 6 hrs then pour into saturated NaHCO$_3$, extract with EtOAc and dry (MgSO$_4$). Filter and concentrate the solution under reduced pressure. Filter the residue through a 4 cm plug of silica gel using 3:1 hexanes:EtOAc as eluant. Concentrate the solution to a foam. Add 1 mL toluene, 1 mL tri-n-butyl tin hydride and 5 mg azobis(2-methylpropionitrile). Heat this solution to 100° C. for 30 min. Without workup, pure 5-tert-butyldimethylsilyl-13-deoxy-23-gem-difluoro-ivermectin aglycone may be obtained following flash chromatography on silica gel.

EXAMPLE 30

13-deoxy-23-gem-difluoro-ivermectin aglycone (30)

Place 25 mg of 5-tert-butyldimethylsilyl-13-deoxy-23-gem-difluoro-ivermectin aglycone, in 3 mL THF at RT and add 1 mL HF.pyridine solution (25 g HF.pyridine, 10 mL pyridine, 25 mL THF) and stir for 12 hrs. Pour the solution into 20 mL 1:1 water:Et$_2$O and separate the layers. Neutralize each layer separately with saturate NaHCO$_3$ ; and extract the aqueous layer with Et$_2$O. Dry (MgSO$_4$) the combined organic layers. Filter the solution and concentrate it under reduced pressure. Pure 13-deoxy-23-gem-difluoro-ivermectin aglycone may be obtained after flash chromatography on silica gel.

EXAMPLE 31

5-tert-butyldimethylsilyl-7-O-trimethylsilyl-23-gem-difluoro-ivermectin aglycone (31)

Dissolve 500 mg of 5-tert-butyldimethylsilyl-23-gem-difluoro-ivermectin aglycone, in 3 mL DMF at RT and add to this 2 mL bis(trimethylsilyl)trifluoroacetamide. Stir the reaction overnight at RT and then purify the product without workup by flash chromatography on silica gel using 85:15 hexanes:EtOAc as eluant. Concentrate the resultant 5-O-tert-butyldimethylsilyl-7,13-bis-O-trimethylsilyl- 23-gem-difluoro-ivermectin aglycone under reduced pressure and to this add 10 mL methanol at RT. Add 5 mg pyridinium p-toluenesulfonate and stir the reaction for 20 min. Pour the solution into 50 mL saturated NaHCO$_3$, extract with methylene chloride and dry (MgSO$_4$). Pure 5-tert-butyldimethylsilyl-7-O-trimethylsilyl-23-gem-difluoro-ivermectin aglycone may be obtained following flash chromatography on silica gel.

EXAMPLE 32

5-tert-butyldimethylsilyl-13-oxo-7-O-trimethylsilyl-23-gem-difluoro-ivermectin aglycone (32)

Dissolve 200 mg of 5-tert-butyldimethysilyl-7-O-trimethylsilyl-23-gem-difluoro-ivermectin aglycone, in 4 mL EtOAc at RT and add to it 300 mg MnO$_2$. Stir the solution for 1 hr, then filter the solution through a bed of Celite and concentrate the solution under reduced pressure. Pure 5-tert-butyldimethylsilyl-13-oxo-7-O-trimethylsilyl-23-gem-difluoro-ivermectin aglycone may be obtained following flash chromatography on silica gel.

EXAMPLE 33

5-tert-butyldimethylsilyl-13-deoxy--7-O-trimethylsilyl-13,23-bis,gem-difluoro-ivermectin aglycone (33)

To 100 mg of 5-tert- butyldimethylsilyl-13-oxo-7-O-trimethylsilyl-23-gem- difluoro-ivermectin aglycone, in 2 mL freshly distilled toluene add 1 mL diethylaminosulfur trifluoride. Heat this solution to 55° C. for four hrs. Quench the reaction by adding it dropwise to an ice-cold saturated NaHCO$_3$ ; solution. Extract with EtOAc and dry (MgSO$_4$). Filter the solution and concentrate under reduced pressure. Preliminary purification may be accomplished by flash chromatography on silica gel using 9:1 hexanes:acetone as eluant. Further purification, if necessary, may be accomplished by preparative reversed phase HPLC (Waters C-18 column, 2.5×30 cm) using 91:9 MeOH:water (v:v) to yield pure 5-tert-butyldimethylsilyl-13-deoxy-7-O-trimethylsilyl-13,23-bis-gem-difluoro-ivermectin aglycone.

EXAMPLE 34

13-deoxy-13,23-bis-gem-difluoro-ivermectin aglycone (34)

Place 25 mg of 5-tert-butyldimethylsilyl-13-deoxy-7-O-trimethylsilyl-13,23-bis-gem-difluoro-ivermectin aglycone, in 3 mL THF at RT and add 1 mL HF.pyridine solution (25 g HF.pyridine, 10 mL pyridine, 25 mL THF) and stir for 48 hrs. Pour the solution into 20 mL 1:1 water:Et$_2$O and separate the layers. Neutralize each layer separately with saturate NaHCO$_3$; and extract the aqueous layer with Et$_2$O. Dry (MgSO$_4$) the combined organic layers. Filter the solution and concentrate it under reduced pressure. Pure 13-deoxy-13,23-bis-gem-difluoro-ivermectin aglycone may be obtained after flash chromatography on silica gel.

EXAMPLE 35

4″,5-bis-O-tert-butyldimethylsilyl-23-gem-difluoro-10,11-dihydro-10hydroxy-7-O-trimethylsilyl-ivermectin (35)

To a solution of 500 mg of 4″,5-bis-O-tert-butyldimethylsilyl-7-O-trimethylsilyl-23-gem-difluoro-ivermectin in 10 mL of acetone and 1 mL water at RT add 110 mg N-bromoacetamide in one portion. Stir the mixture for 1 hr in the dark and work up by the addition of water and extraction with Et$_2$O. Dry (MgSO$_4$), filter, remove the solvent under reduced pressure and purify the product by flash chromatography on silica gel to afford crude 11-bromo-4″,5-bis-O-tert-butyldimethylsilyl-23-gem-difluoro-10-hydroxy-7-O-trimethylsilyl-ivermectin. Dissolve this intermediate in 6 mL toluene and add 1 mL tri-n-butyl tin hydride. Heat this solution to 100° C. for 1 hr. Pure 4'',5-bis-O-tert-butyldimethylsilyl-23-gem-difluoro-10,11-dihydro-10-hydroxy-7-O-trimethyl silyl-ivermectin may be obtained by flash chromatography on silica gel without workup.

EXAMPLE 36

4'',5-bis-O-tert-butyldimethylsilyl-23-gem-difluoro-10,11-dihydro-10-fluoro-7-O-trimethylsilyl-ivermectin (36)

Cool 200 mg of 4'',5-bis-O-tert-butyldimethylsilyl-23-gem-difluoro-10,11-dihydro-10-hydroxy-7-O-trimethylsilyl-ivermectin, to $-78°$ C. in 5 mL methylene chloride. To this mixture add dropwise 0.10 mL diethylaminosulfur trifluoride. After 1 hour at $-78°$ C. quench the reaction with 5 mL of a 7% aqueous sodium carbonate solution. Extract the product with methylene chloride, dry ( $MgSO_4$), filter and concentrate the solution under reduced pressure. Pure 4'',5-bis-O-tert-butyldimethylsilyl-23-gem-difluoro-10,11-dihydro-10-fluoro-7-O-trimethylsilyl-ivermectin may be obtained following flash chromatography on silica gel.

EXAMPLE 37

23-gem-difluoro-ivermectin (37)

Place 50 mg of 4'',5-bis-O-tert-butyldimethylsilyl-23-gem-difluoro-10,11-dihydro-10-fluoro-7-O-trimethylsilyl-ivermectin, in 3 mL THF at RT and add 1 mL HF.pyridine solution (25 g HF.pyridine, 10 mL pyridine, 25 mL THF) and stir for 48 hrs. Pour the solution into 20 mL 1:1 water:$Et_2O$ and separate the layers. Neutralize each layer separately with saturate $NaHCO_3$ and extract the aqueous layer with $Et_2O$. Dry ($MgSO_4$) the combined organic layers. Filter the solution and concentrate it under reduced pressure. Pure 23-gem-difluoro-10-fluoro-ivermectin may be obtained after flash chromatography on silica gel.

EXAMPLE 38

5-tert-butyldimethylsilyl-13-deoxy-23-gem-difluoro-13-fluoro-7-O-trimethylsilyl-ivermectin aglycone (38)

Cool 200 mg of 5-tert-butyldimethylsilyl-7-O-trimethylsilyl-23-gem-difluoro-ivermectin aglycone to $-78°$ C. in 5 mL methylene chloride. To this mixture add dropwise 0.10 mL diethylamino-sulfur trifluoride. After 1 hour at $-78°$ C. quench the reaction with 5 mL of a 7% aqueous sodium carbonate solution. Extract the product with methylene chloride, dry ($MgSO_4$), filter and concentrate the solution under reduced pressure. Pure (38) may be obtained following flash chromatography on silica gel.

Pure 5-O-tert-butyldimethylsilyl-7-O-trimethylsilyl-13-deoxy-13-fluoro-23-gem-difluoro-ivermectin aglycone may be obtained through a similar process except that the starting material is 5-O-tert-butyldimethylsilyl-7-O-trimethylsilyl-23-oxo-ivermectin aglycone. Additionally, to the chilled solution of methylene chloride is added 400 ml diethylaminosulfur trifluoride. The solution is then slowly warmed to RT over the course of one hour and then heated to 35° C. for 12 hours. Quench the reaction by adding it dropwise to an ice-cold solution of saturated $NaHCO_3$, extract with ethyl acetate and dry ($MgSO_4$). Filter and concentrate the solution under reduced pressure, followed by flash chromatography on silica gel.

EXAMPLE 39

13-deoxy-23-gem-difluoro-13-fluoro-ivermectin aglycone (39)

Place 50 mg of 5-tert-butyldimethylsilyl-13-deoxy-23-gem-difluoro-13-fluoro-7-O-trimethylsilyl-ivermectin aglycone, in 3 mL THF at RT and add 1 mL HF.pyridine solution (25 g HF.pyridine, 10 mL pyridine, 25 mL THF) and stir for 48 hrs. Pour the solution into 20 mL 1:1 water:$Et_2O$ and separate the layers. Neutralize each layer separately with saturated $NaHCO_3$; and extract the aqueous layer with $Et_2O$. Dry ($MgSO_4$) the combined organic layers. Filter the solution and concentrate it under reduced pressure. Pure 13-deoxy-23-gem-difluoro-13-fluoro-ivermectin aglycone may be obtained after flash chromatography on silica gel.

EXAMPLE 40

25-des(2-butyl)-25-methyl-5-tert-butyldimethylsilyl-7)-trimethylsilyl-avermectin aglycone (40)

Dissolve 50 mg of 25-des(2-butyl)-25-methyl-avermectin aglycone in 2 mL dimethylformamide at RT and add 25 mg imidazole and 27 mg tert-butyldimethylsilyl chloride. Stir the solution for 1 hr and then pour it into water. Extract with EtOAc, dry ($MgSO_4$), filter and concentrate the solution under reduced pressure. Pure 25-des(2-butyl)-25-methyl-5-tert-butyldimethylsilyl-avermectin aglycone may be obtained following flash chromatography on silica gel. Dissolve 500 mg of this compound in 3 mL DMF at RT and add to this 2 mL bis(trimethylsilyl)trifluoroacetamide. Stir the reaction overnight at RT and then purify the product without workup by flash chromatography on silica gel using 85:15 hexanes:EtOAc as eluant. Concentrate the resultant 5-O-tert-butyldimethyl-silyl-25-des(2-butyl)-25-methyl-7,13-bis-O-trimethylsilyl-avermectin aglycone under reduced pressure and to this add 10 mL methanol at RT. Add 5 mg pyridinium p-toluene-sulfonate and stir the reaction for 20 min. Pour the solution into 50 mL saturated $NaHCO_3$, extract with methylene chloride and dry ($MgSO_4$). Pure 25-des(2-butyl)-25-methyl-5-tert-butyldimethylsilyl-7-O-trimethylsilyl-avermectin aglycone may be obtained following flash chromatography on silica gel.

EXAMPLE 41

25-des(2-butyl)-25-methyl-5-tert-butyldimethylsilyl-13-deoxy-13-gem-difluoro-7-O-trimethylsilyl-avermectin aglycone (41)

Dissolve 400 mg of 25-des(2-butyl)-25-methyl-5-tert-butyldimethylsilyl-7-O-trimethylsilyl-avermectin aglycone, in 3 mL methylene chloride at RT and add to this solution 275 mg Dess-Martin reagent. After 10 min, purify the reaction without workup by flash chromatography on silica gel using 9:1 hexanes:acetone as eluant to yield pure enone, 25-des(2-butyl)-25-methyl-5-tert-butyldimethylsilyl13-oxo-7-O-trimethylsilyl-avermectin aglycone. To 100 mg of the enone in 2 mL freshly distilled toluene add 1 mL diethylaminosulfur trifluoride. Heat this solution to 55° C. for four hrs. Quench the reaction by adding it dropwise to an ice-cold saturated $NaHCO_3$; solution. Extract with EtOAc and dry ($MgSO_4$). Filter the solution and concentrate under reduced pressure. Preliminary purification may be accomplished by flash chromatography on silica gel using 9:1 hexanes:acetone as eluant. Further purification, if necessary, may be accomplished by preparative reversed phase HPLC (Waters C-18 column, 2.5×30 cm) using 91:9 MeOH:water (v:v) to yield pure 25-des(2-butyl)-25-methyl-5-tert-butyldimethylsilyl-13-deoxy-13-gem-difluoro-7-O-trimethylsilyl-avermectin aglycone.

EXAMPLE 42

25-des(2-butyl)-25-methyl-13-deoxy-13-gem-difluoro-avermectin aglycone (42)

Place 50 mg of 25-des(2-butyl)-25-methyl-5 -tert-butyldimethylsilyl-13-deoxy-13-gem-difluoro-7-O-trimethylsilyl-avermectin aglycone, in 3 mL THF at RT and add 1 mL HF.pyridine solution (25 g HF.pyridine, 10 mL pyridine, 25 mL THF) and stir for 48 hrs. Pour the solution into 20 mL 1:1 water:Et$_2$O and separate the layers. Neutralize each layer separately with saturate NaHCO$_3$; and extract the aqueous layer with Et$_2$O. Dry (MgSO$_4$) the combined organic layers. Filter the solution and concentrate it under reduced pressure. Pure 25-des(2-butyl)-25-methyl-13-deoxy-13-gem-difluoro- avermectin aglycone(42) may be obtained after flash chromatography on silica gel.

EXAMPLE 43

25-des(2-butyl)-25-cyclohexyl-13-deoxy-13-gem-difluoro-avermectin aglycone (43)

Starting with 50 mg of 25-des(2-butyl)-25-cyclohexyl-avermectin aglycone, compound 25-des(2-butyl)-25-cyclohexyl-13-deoxy-13-gem-difluoro-avermectin aglycone may be obtained by following the procedures set forth in Examples 40 thru 42.

EXAMPLE 44

25-des(2-butyl)-25-phenyl-13-deoxy-13-gem-difluoro-avermectin aglycone (44)

Starting with 25-des(2-butyl)-25-phenyl avermectin aglycone, compound 25-des(2-butyl)-25-phenyl-13-deoxy-13-gem-difluoro-avermectin aglycone may be obtained by following the procedures set forth in Examples 40 thru 42.

EXAMPLE 45

13-deoxy-13-gem-difluoro-25des(2-butyl)-25-[2-(4-methylpent-2-enyl)]-avermectin aglycone (45)

Starting with 25-des(2-butyl)-25-[2(4-methylpent-2-enyl)]-avermectin, compound 13-deoxy-13-gem-difluoro-25-des(2-butyl)-25-[2-(4-methylpent-2-enyl)]-avermectin aglycone(45) may be obtained by following the procedures set forth in Examples 40 thru 42.

What is claimed is:
1. A compound having the formula:

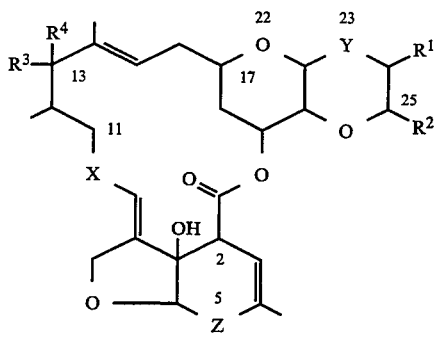

Wherein:
Y is: —CF$_2$—;
R$^1$ is:
 (a) —H, or
 (b) —CH$_3$;
R$^2$ is:
 (a) —H,
 (b) —C$_1$-C$_8$ alkyl,
 (c) —C$_3$-C$_8$ cycloalkyl,
 (d) —C$_2$-C$_8$ alkenyl,
 (e) —C$_3$-C$_8$ cycloalkenyl, or
 (f) —aryl;
Z is:
 (a) —CH(OH)—,
 (b) —CO—
 (c) —CH(OCH$_3$)—
 (d) —C(=NOH)—, or
 (e) —C(=NOCH$_3$)—;
R$^3$ is:
 (a) —H,
 (b) —(C$_1$-C$_8$ alkoxy)$_n$ wherein n=1, 2, or 3;

(c)

(d)

Wherein:
A is:
 (a) —CF$_2$—,
 (b) —CH(OH)—,
 (c) —CHNR$^5$R$^{5A}$—, or
 (d) —CHSR$^6$—;
R$^5$ and R$^{5A}$ are independently;
 (a) H,
 (b) C$_1$-C$_8$ alkyl
 (c) C$_1$-C$_6$ alkenyl, or
 (d) C$_1$-C$_6$ alkanoyl;
R$^6$ is:
 (a) C$_1$-C$_3$ alkoxyaminoalkyl, or
 (b) C$_1$-C$_3$ alkylNR$^5$R$^{5A}$;

R⁴ is:
  (a) —H, or
  (b) —F;
X is:
  (a) —CH₂—,
  (b) =CH—(10, 11 double bond),
  (c) —CH(OH)—, or
  (d) —CHF—.

2. The compound of claim 1 wherein:
Y is —CF₂—;
R¹ is:
  (a) —H, or
  (b) —CH₃;
R² is:
  (a) —H,
  (b) sec-butyl, isopropyl, ethyl,
  (c) cyclohexyl, cyclopentyl,
  (d) 2-(4-methylpent-2-enyl), or
  (e) phenyl;
Z is:
  (a) —CH(OH)—,
  (b) —C(OCH₃)—,
  (c) —C(=NOH)—, or
  (d) —C(=NOCH₃)—;
R³ is:
  (a) —H
  (b) —F (if R⁴ is H),
  (c) —OCH₂OCH₃,
  (d) —OCH₂OCH₂CH₂OCH₃)—, (e)
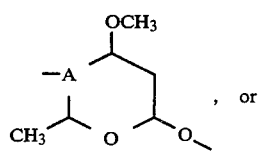
, or

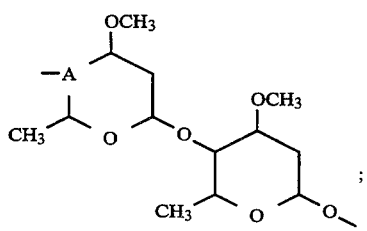
;

Wherein:
A is:
  (a) —CH(OH)—,
  (b) —CHNCH₂CH₃,
  (c) —CHSCH₂CH₂NOCCH₃, or
  (d) —CF₂—;
R⁴ is:
  (a) —H, or
  (b) —F (if R³ is other then F);
X is:
  (a) —CH₂—,
  (b) =CH—(10, 11 double bond),
  (c) —CH(OH)—, or
  (d) —CHF—.

3. The compound of claim 2 wherein:
Y is —CF₂—;
R¹ is —CH₃;
R² is:
  (a) sec-butyl, or
  (b) isopropyl;
Z is:

(a) —CH(OH)—, or
  (b) —C(=NOH)—;
R³ is:
  (a) —H,
  (b) OCH₂OCH₃, or
  (c) OCH₂OCH₂CH₂OCH₃;
R⁴ —F—;
X is =CH—(10, 11 double bond).

4. The compound of claim 1 wherein:
R³ is:

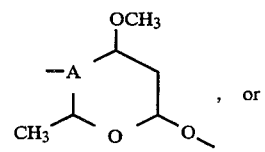
, or

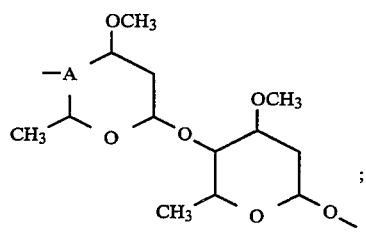
;

Wherein:
A is —CF₂—;
R⁴ is —H;
Y is:
  (a) —CH₂—,
  (b) =CH—(22, 23 double bond),
  (c) —CH(OH)—,
  (d) —C(=NOH)—,
  (e) —C(=NOCH₃), or
  (f) —CF₂—,
R¹ is —CH₃;
R²is:
  (a) sec-butyl, isopropyl, ethyl,
  (b) cyclohexyl, cyclopentyl,
  (c) 2-(4-methylpent-2-enyl), or
  (d) phenyl;
Z is:
  (a) —CH(OH)—,
  (b) —CO—,
  (c) —CH(OCH₃)—,
  (d) —C(=NOH—), or
  (e) —C(=NOCH₃—);
X is:
  (a) —CH₂—,
  (b) =CH—(10, 11 double bond),
  (c) —CH(OH)—, or
  (d) —CHF—.

5. The compound of claims 4 wherein:
R³ is:

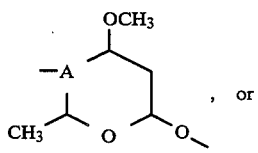
, or

-continued

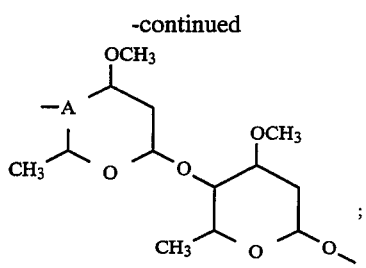

Wherein:
A is —CF$_2$—;
R$^4$ is H
Y is:
(a) —CH$_2$—, (b) =CH—(22, 23 double bond),
(c) —CH(OH)—, or
(d) —C(=NOCH$_3$);
R$^1$ is —CH$_3$;
R$^2$ is:
(a) sec-butyl, or
(b) isopropyl;
Z is:
(a) —CH(OH)—, or
(b) —C(=NOH)—;
X is =CH—(10, 11 double bond).

6. A composition useful for the treatment or prevention of parasitic infections of animals which is comprised of an inert carrier and a compound of claim 1.

7. A composition useful for the treatment of pests of plants which is comprised of an inert carrier and a compound of claim 1.

* * * * *